United States Patent [19]
King et al.

[11] Patent Number: 5,369,251
[45] Date of Patent: Nov. 29, 1994

[54] MICROWAVE INTERSTITIAL HYPERTHERMIA PROBE

[75] Inventors: Ray J. King; Karl V. King, both of Pleasanton, Calif.

[73] Assignee: KDC Technology Corp., Livermore, Calif.

[21] Appl. No.: 944,947

[22] Filed: Sep. 14, 1992

[51] Int. Cl.$^5$ .............................................. H05B 6/72
[52] U.S. Cl. .................................. 219/695; 219/696; 219/690; 607/116; 607/156
[58] Field of Search ................ 219/10.55 A, 10.55 F, 219/10.55 R, 10.81, 690, 679, 695, 691, 694, 696, 770, 746, 748; 607/116, 156

[56] References Cited

U.S. PATENT DOCUMENTS

| | | | |
|---|---|---|---|
| 4,612,940 | 9/1986 | Kasevich et al. | 607/154 |
| 4,700,716 | 10/1987 | Kasevich et al. | 219/10.55 F |
| 4,841,988 | 6/1989 | Fetter et al. | 219/10.55 F |
| 4,945,912 | 8/1990 | Langberg | 128/401 |
| 5,026,959 | 6/1991 | Ito et al. | 219/10.55 A |
| 5,234,004 | 8/1993 | Hascoet et al. | 607/116 |

OTHER PUBLICATIONS

Ryan, T. P., "Techniques for Heating Brain Tumors with Implanted Microwave Antennas," 1991 IEEE MIT-S Digest, pp. 791–794.

Hurter, W., et al., "A Dipole Antenna for Interstitial Microwave Hyperthermia", IEEE Trans. MIT-39(6), Jun. 1991 pp. 1048–1054.

Tumeh, A. M. & M. F. Iskander, "Performance Comparison of Available Interstitial Antennas for Microwave Hyperthermia," IEEE Trans. Mtt-37(7), 1989 pp. 1126–1133.

Iskander, M. F. et al., "Evaluation and Optimization of the Electromagnetic Performance of Interstitial Antennas for Hyperthermia," Inst. J. Radiation Oncology Biol. Phys., 18, 1990, pp. 895–902.

Primary Examiner—Philip H. Leung
Attorney, Agent, or Firm—Henry P. Sartorio

[57] ABSTRACT

Method and apparatus for in vivo or in vitro selective deposition of microwave power patterns in lossy dielectric materials, particularly biological tissue. Configured as a needle-like probe, a miniature coaxial cable (1) having a circumferential gap (12) in the shield (2) is wrapped with an electrically thin dielectric substrate (18). The cable center conductor (6) extends immediately past gap (12) and is shorted to cable shield (2). A thin conductive dipole resonator (21) is positioned on substrate (18) and over gap (12) to achieve inductive coupling between the cable center conductor (6) and the dipole resonator (21) through gap (12). The ends of the dipole resonator (21) are capacitively (22) loaded so as to make the current on resonator (37) more uniform and to greatly reduce and stabilize the resonant frequency to be essentially insensitive to the dielectric properties of the surrounding material. A thin metal strip (27) is positioned on first superstrate (23) over and parallel to resonator (21), to diminish the hot spot near feed gap (12) and to make coupling to the surrounding lossy material (7) along the length of resonator (21) more uniform. Second superstrate (33), which could be a dielectric catheter, covers the entire probe assembly (30).

25 Claims, 3 Drawing Sheets

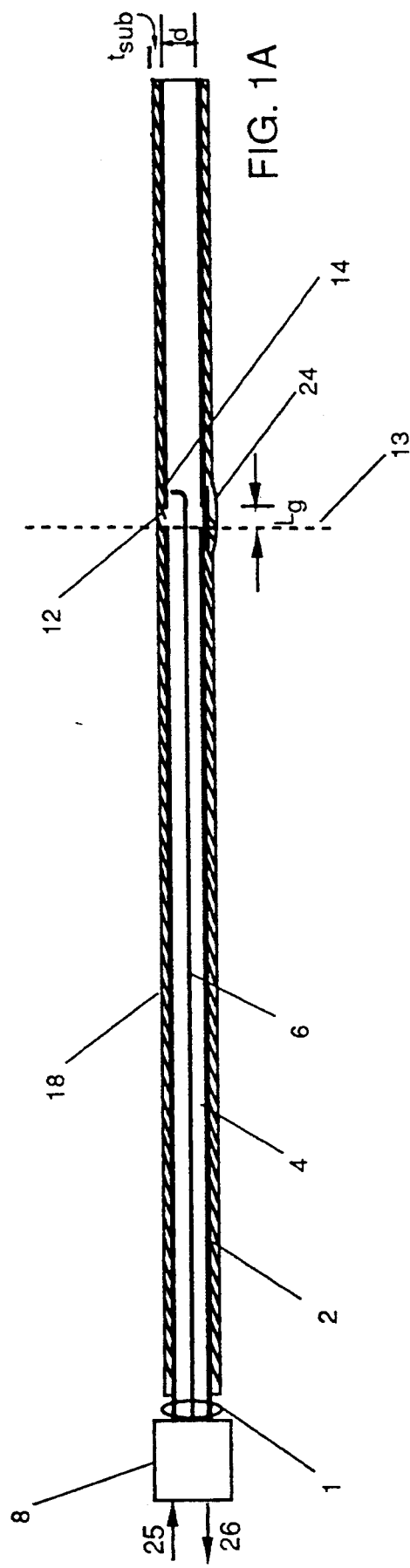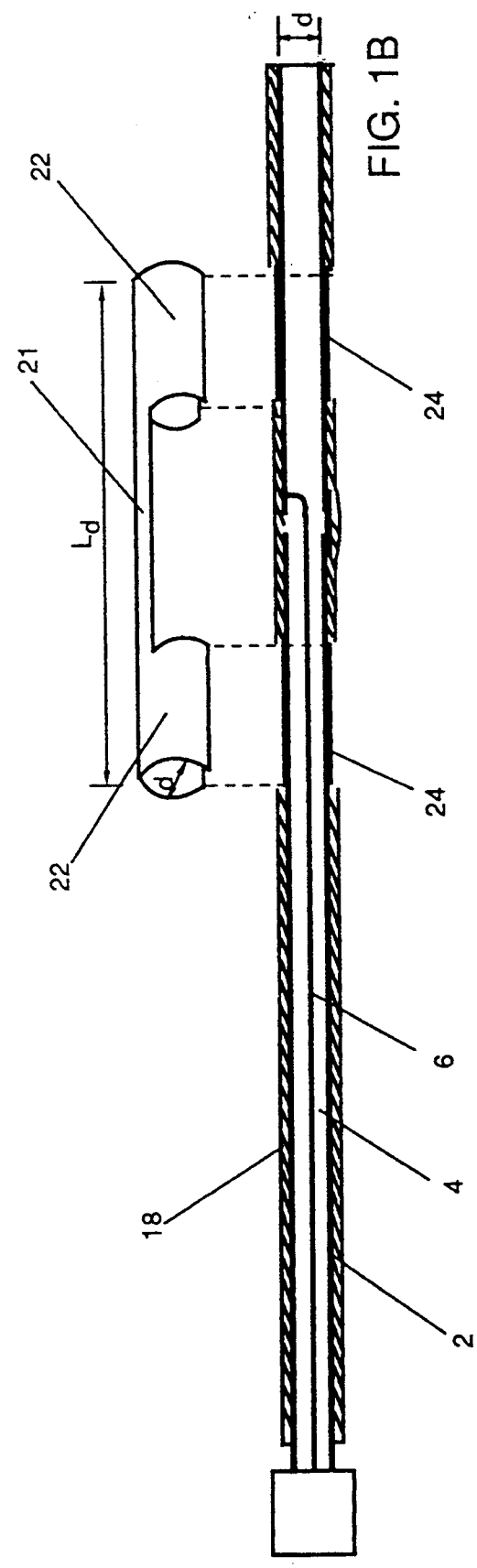

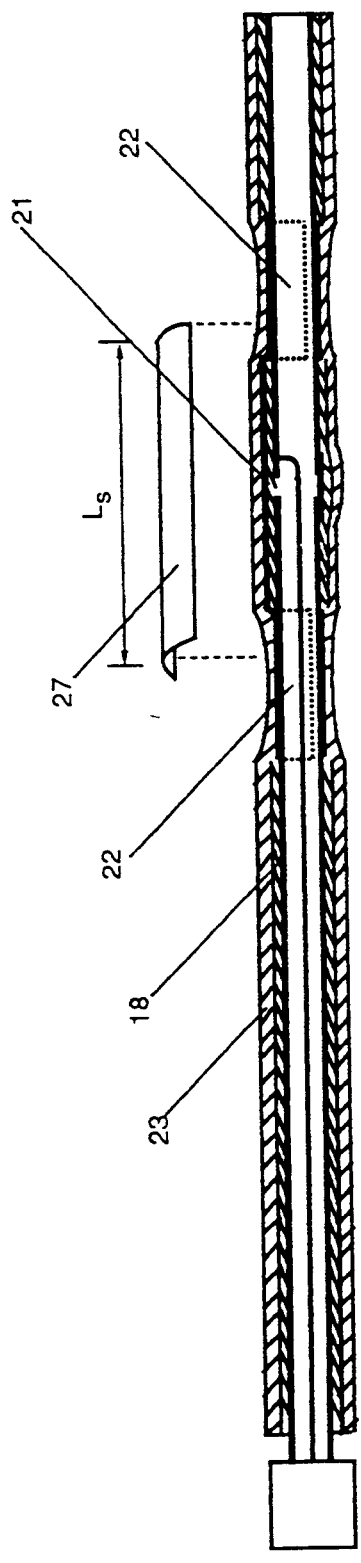
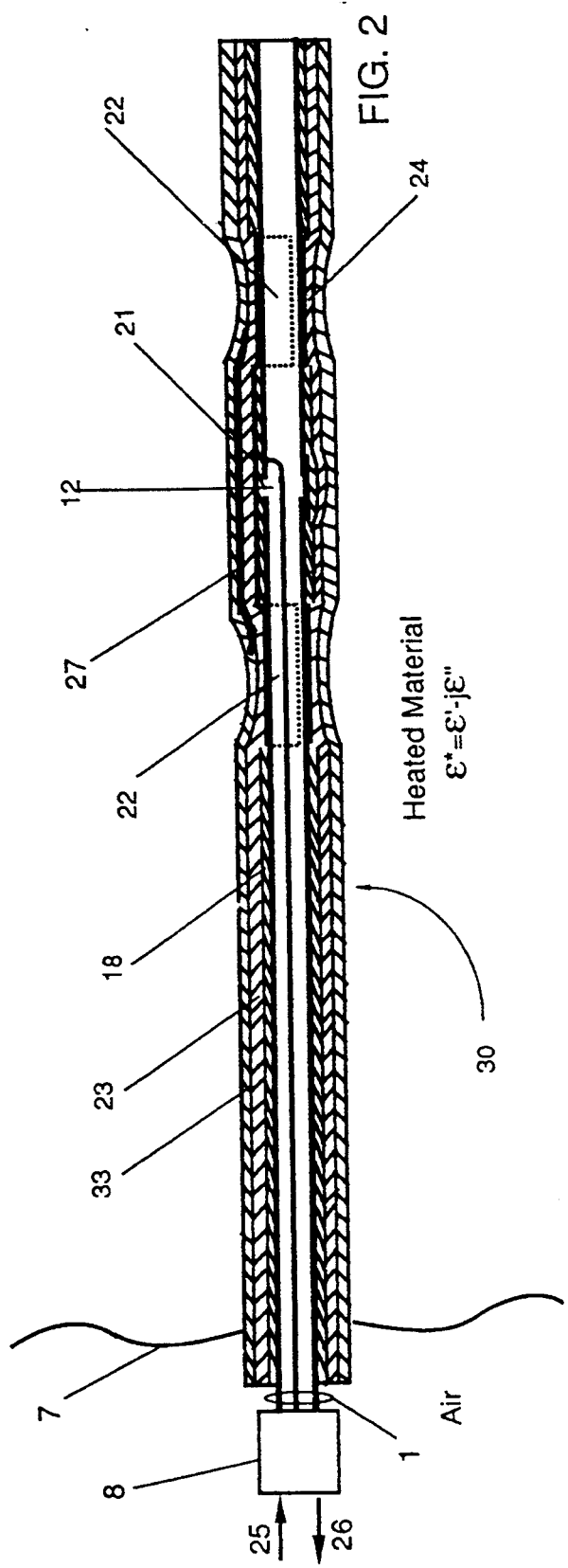

MICROWAVE INTERSTITIAL HYPERTHERMIA PROBE

GOVERNMENT RIGHTS

This invention was made with Government support under Grant 1 R43 CA 53941-01 awarded by the National Institutes of Health. The Government has certain rights in the invention.

BACKGROUND - FIELD OF INVENTION

This invention relates to the construction and use of needle-like microwave interstitial probe antennas for selective in vivo or in vitro deposition of microwave power patterns in lossy dielectric media, particularly into biological tissue.

BACKGROUND - DISCUSSION OF PRIOR ART

The invention relates to the construction and use of needle-like probe antennas as interstitial applicators of microwave power for the purpose of selective heating. Microwave interstitial probe antennas are clinically used in the treatment of nonoperable cancer tumors, wherein the probe or an array of probes is invasively inserted into the tumor. Upon the application of microwave power at the frequency at which the antenna is resonant, the cancer cells can be heated and sustained at temperatures in the 42°–50° C. range (hyperthermia) causing the cells to lose their ability to divide. Moreover, hyperthermia is synergistic with radiation therapy and chemotherapy with the result that the effectiveness of these modalities are enhanced. Radiation alone requires about twice the duration compared to combined radiation and hyperthermia, and the exposure duration is reduced by half. Thus, there is strong motivation for hyperthermia techniques that can heat entire tumors locally, without damaging the surrounding healthy tissue.

Another important application of interstitial hyperthermia probe antenna is in Trans-Urethral Restructural Procedures (TURP) for treatment of enlarged prostates. The applicator probe is noninvasively inserted directly into the prostate via the urethral canal. Depending on the power deposition pattern and time of exposure, an enlarged prostate can be heated to create lesions deep within the prostate pulp, with subsequent reduced constriction of the urethra upon healing. The procedure has numerous merits compared to traditional prostatectomy; chiefly the procedure is non surgical and it can be done out patient with minimal medication. As a result, the cost is only a fraction of surgical prostatectomy, recovery is more rapid, and the long term success is substantially greater. The technique would also appear to be applicable to prostate cancer and chronic prostatitis, combined with Rx medication.

Of primary importance in the design of such applicators is the roughly ellipsoidal volume of effective heating around the antenna, and the uniformity of heating, i.e., the avoidance of excessive heating at local "hot spots" along the antenna length. It is known that heating is most uniform when an applicator antenna is resonant, but resonant antennas often suffer from hot spots at the antenna tip and the feed point. Also, the radius of effective power penetration increases with decreasing frequency, but decreasing the frequency typically requires longer antennas. Ideally, a miniaturized antenna which is only a small fraction of a half wavelength in air (i.e., 2.5 to 5 cm long) is desired, and the power deposition to the surrounding tissue should be uniform without hot spots along the antenna length.

Initial microwave interstitial probes were simply bare antennas, the antenna stub being a quarter wavelength long extension of the center conductor of a miniature coaxial cable (the so-called Darmouth Dipole Antenna). When inserted into the material to be heated (e.g., a tumor), these applicators have several disadvantages:

due to stray induced currents on the feed cable shield, the heating pattern along the antenna depends on the insertion depth from the air-medium interface, heating along the antenna length is nonuniform, resulting in hot spots at the feed and/or at the antenna tip, the frequency of operation is restricted by the allowable stub length, and the impedance match between the feed cable and the stub is often poor and unpredictable. This affects the antenna efficiency.

To overcome these problems, numerous designs have been proposed [Ryan, IEEE MTT-S Digest, 1991, pp. 791–794]. The choke dipole [Hurter, Reinbold and Lorenz, IEEE Trans. MTT 39(6), June 1991, pp. 1048–1054] was introduced to counter the effect of stray return currents on the shield of the feed cable, and thereby minimize the effects of insertion depth on the heating pattern. The antenna has also been made in the form of a helix to reduce the resonant frequency and shield currents. The modified choke dipole combines the features of the other antennas.

Recent experience has shown that insulated antenna probes produce more uniform power deposition and temperature distributions locally within the tissue surrounding the probe. The wall thickness of the insulating sheath (e.g., a catheter) has proven to be a critical parameter for improving power deposition and for minimizing hot spots. For a comparative summary of the state of the art for microwave interstitial antennas, including the use of an insulating sheath, see [Tumeh and Iskander, IEEE Trans. on Microwave Theory and Techniques, MTT-37(7), July, 1989, pp. 1126–1133.]Insulated multi-section antennas, each section having its own characteristic impedance and rate of power coupling to the heated medium, have been proposed by Iskander, Tumeh and Furse [Int'l. J. Radiation Oncology Biol. Phys., Vol. 18, 1990, pp. 895–902], with the objective of improving the deposition of microwave power along the antenna length, improving the input impedance match, and lowering the resonant frequency.

Prior art shows no methods for simultaneously addressing all of the difficulties alluded to above.

SUMMARY OF THE INVENTION

The invention is method and apparatus for needle-like resonant probes for selective deposition of microwave power and heating patterns within lossy dielectric materials, particularly for use as a microwave hyperthermia applicator.

In its most basic form the invention is constructed as a dipole resonator antenna which is positioned parallel and adjacent to, and electrically insulated from, a miniature coaxial feed cable. The dipole antenna is inductively coupled to the microwave power in the coaxial cable by means of a small circumferential gap cut in the cable shield. By coupling the gap to the dipole at its center, currents are induced on the dipole in a balanced and symmetric manner. With proper design of the feed gap, the dipole impedance can be well matched to the coaxial cable with very small reflection from the gap at the resonant frequency of the dipole.

The interstitial probe invention is specifically designed to:

(a) miniaturize the antenna length and also to achieve a much lower resonant frequency, thereby improving the effective radial depth of power penetration into the heated medium, (b) achieve maximally uniform coupling to the surrounding medium along the active portion of the antenna length, without hot spots or power-starved regions, (c) achieve an exceptionally high antenna efficiency, stable resonant frequency and good impedance match when the probe is inserted into the material to be heated, and (d) minimize stray currents on the cable shield so that, among other effects, the deposited power pattern does not depend on the depth of probe insertion into the medium being heated.

To achieve these desired properties, the dipole resonator is capacitively loaded at both ends. This greatly reduces the resonant frequency for a given dipole length (miniaturization property (a) above), and makes the current distribution along the dipole much more uniform. To further improve the uniformity of the coupled power from the dipole to the surrounding medium (uniform coupling property (b) above), a thin metal strip is placed over the dipole center section, electrically insulated from the dipole. This has the effect of suppressing coupling to the surrounding medium near the feed point at the dipole center, and provides a lower attenuation path for power flow toward both ends of the dipole. The capacitive loading feature also causes the resonant frequency ($f_r$) to be highly stable, irrespective of the real dielectric constant of the surrounding medium. And with the proper degree of inductive coupling between the feed gap and the dipole, a good impedance match is achieved when the probe is inserted into the lossy material (tissue) to be heated. Due to negligible reflected power from the antenna feed, this causes the probe to be highly efficient (property (c) above). Conversely, when the probe is withdrawn from the tissue, the impedance match is poor, automatically resulting in low antenna efficiency and little radiation into the environment. Finally, probe insertion depth effects (property (d) above) are inherently minimized because the electrically insulated resonant dipole is the active device, rather than having a portion of the coaxial cable as the resonator. In other words, stray return currents are closely confined to the cable in the immediate proximity to the dipole, and do not extend appreciably along the cable to the air-material interface.

OBJECTS AND ADVANTAGES

Accordingly, the following objects and advantages are claimed:

The invention provides a needle-like microwave resonant probe antenna for selective deposition of microwave power patterns in lossy dielectric media, in particular for microwave in vivo interstitial hyperthermia treatment of bio-tissue. Miniaturization of the antenna is achieved by capacitively loading the dipole resonator to resonate at a low microwave frequency and thereby achieve maximum power (heating) penetration in the radial direction from the probe. This method also greatly increases the resonator quality factor (Q), and causes the resonant frequency to be exceedingly stable, irrespective of the real permittivity of the surrounding tissue.

A further advantage is that the heating pattern can be made uniform along the active dipole length by suppressing the hot spot near the dipole feed while increasing heating in the region between the feed and the dipole ends. This also causes the field in the heated medium to become a cylindrically expanding wave with smooth, predictable phase contours. Such well-predictable phase contours are desirable when positioning an array of probe antennas in the medium to be heated to achieve more uniform heating throughout a given volume.

Another advantage is that when the probe is inserted into biological tissue there is an exceptionally good impedance match at the probe input at the resonant frequency of the resonator. This results in a high probe efficiency since the reflected power is negligible. When the probe is located in air, it is no longer resonant and there is little radiation into the environment.

A further advantage of the probe is that the heating pattern is independent of the distance from the air-heated medium interface. This is attributed to the fact that only the dipole is resonant and active, with the result that stray return currents on the exterior of the coaxial feed cable shield are greatly suppressed.

DESCRIPTION OF DRAWINGS

The characteristics and advantages of the invention will appear from the following description illustrated by the figures which show:

FIGS. 1A, 1B and 1C Cross section assembly views of needle-like resonant probe antenna for deposition of microwave power and heating patterns within a glossy dielectric material, showing progressive stages in the probe assembly.

FIG. 2: Cross section of assembled resonant probe antenna for deposition of microwave power and heating patterns within a lossy dielectric material.

In FIGS. 1A, 1B, 1C, 2, 3A and 3B the diameters of the probe antenna have been greatly expanded to show construction detail.

LIST OF REFERENCE NUMERALS

Figure 3B:
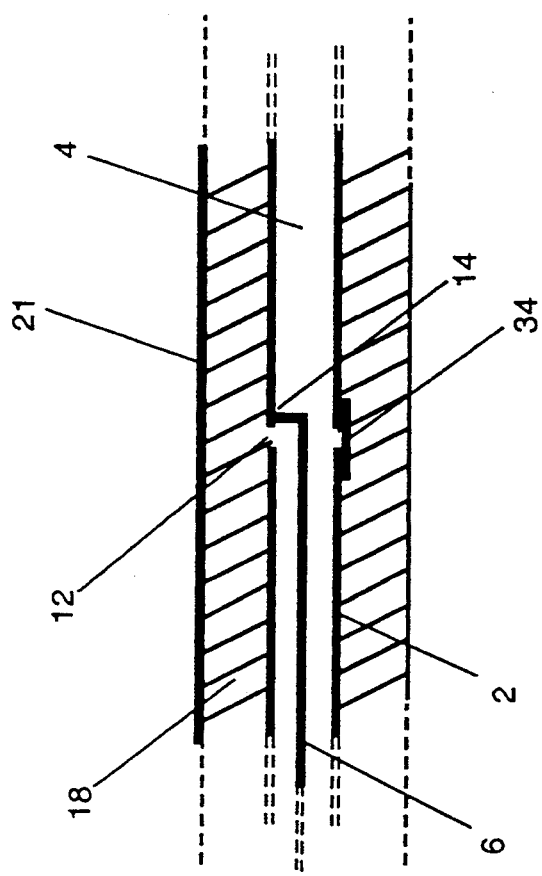
FIGS. 3A and 3B Partial longitudinal cross section views of the probe antenna showing detail of methods for reducing coupling between the feed gap and the resonator using (A) a coupling reducer strip (baffle), and (B) a resistive wire bridge.

1. Miniature coaxial cable
2. Outer conducting shield of miniature coaxial cable 1 of diameter d
4. Dielectric core (e.g., Teflon ®) of miniature coaxial cable 1
6. Center conductor of coaxial cable 1
7. Heated material (tissue) having complex dielectric constant $\epsilon^* = \epsilon' - \epsilon''$
8. SMA or other suitable connector to probe antenna 30
12. Circumferential feed gap of length $L_g$ in the outer conducting shield 2 of miniature coaxial cable 1
3. Reference plane at the input to feed gap 12
14. Short circuit connection of coaxial cable center conductor 6 to outer shield 2
18. Thin dielectric substrate of wall thickness $t_{tub}$ which electrically insulates dipole resonator 21 from cable shield 2

19. Thin dielectric substrate for insulating coupling reducer 32 from cable shield 2
21. Conductive dipole resonator of length $L_d$ and width $w_d$ having capacitive loading 22 at both ends
22. Capacitive loading at ends of dipole 21
23. Thin first dielectric superstrate covering dipole 21 and end capacitors 22
24. Very thin dielectric substrate insulator separating capacitors 22 from coaxial cable shield 2
25. Incident wave
26. Reflected wave
27. Conductive strip of length $L_s$ positioned over dipole 21 and first dielectric superstrate 23
30. Final resonant probe assembly for heating material 7
32. Conductive coupling reducer strip or baffle of length $L_b$ and width $w_b$.
33. Second dielectric superstrate (e.g., catheter) which electrically insulates conductive strip 27 from heated material 7
34. Resistive wire bridge which extends across gap 12 to regulate inductive coupling between gap 12 and dipole 21

OPERATION OF THE INVENTION

Referring now to the drawings, FIGS. 1A, 1B and 1C show the progressive construction of the probe antenna invention to arrive at the final composite form 30 shown in FIG. 2. The basic form of the probe in FIG. 1A is comprised of a miniature coaxial cable 1 having outer conducting shield 2 of diameter d, center conductor 6 and core dielectric 4. A narrow (electrically short) circumferential gap 12 is formed in shield 2 entirely around cable 1. Connector 8 is provided to connect probe 30 to a suitable microwave frequency source of sufficient output power to heat the material 7 surrounding probe 30. Cable center conductor 6 is shorted to the extension of shield 2 at point 14 just beyond gap 12 so as to create a large current and corresponding magnetic field at gap 12. A cylindrical substrate 18, such as Teflon ® heat-shrink tubing of thickness $t_{tub}$ covers Cable 1, including gap 12. In FIG. 1B, a dipole resonator 21 is placed on substrate 18 over gap 12. The function of substrate 18 is to electrically insulate dipole resonator 21 from cable shield 2.

Dipole resonator 21 is fabricated as a metal foil of length $L_d$ and width $w_d$, having two cylindrical capacitors 22 formed at its ends. Substrate 18 is cut away from cable shield 2 inside of capacitors 22, and in its place very thin dielectric substrate insulators 24 are wrapped around cable shield 2. For example, insulator 24 could be a very thin (e.g., 0.0005 inches) Mylar ® or Teflon ® film. The intended purpose of capacitors 22 and thin substrate 24 is to greatly increase the capacitance at the ends of dipole 21, thereby making the current uniform along the length of dipole 21. Such capacitive loading also has the effect of greatly reducing the resonant frequency ($f_r$) of dipole 21.

With dipole 21 having end capacitors 22 properly positioned, a first superstrate 23 is now added over substrate 18 as shown in FIG. 1C. To hold dipole 21 and capacitors 22 firmly in place, first superstrate 23 could be heat-shrink Teflon ® which tightly grips and insulates the dipole resonator assembly. To further distribute the microwave energy along dipole 21, a metal foil strip 27 of length $L_s$ ($<L_d$) and width $w_s$ which is comparable to the width $w_d$ of dipole 21 is centered over dipole 21, extending partially over end capacitors 22 as also shown in FIG. 1C. This strip 27 has the effect of diminishing the coupled power delivered to heated material 7 in the immediate vicinity of feed gap 12, and to fill in the coupled power at points between gap 12 and the ends of capacitors 22. Finally, second superstrate 33 is added over the entire assembly to insulate strip 27 from the heated material 7 as shown in the complete assembly 30 in FIG. 2. Second superstrate 33 could be a catheter into which the remainder of the probe assembly is inserted.

Capacitors 22 serve three purposes. First, they cause the current distribution along the narrow section of dipole 21 to be nearly uniform, but rapidly tapering to zero at the capacitor ends. Second, the additional capacitance substantially reduces the resonant frequency of dipole 21 for a given dipole length $L_d$. Thus, resonant frequencies of the order of 300-700 MHz are possible for dipole lengths of the order of only 4 cm long. This greatly increases the depth of power penetration into material 7, particularly in the radial direction outward from the surface of probe assembly 30. Third, the large capacitance of capacitors 22 serves to make the resonant frequency very stable, independent of surrounding real permittivity of material 7.

Many desirable effects of capacitors 22 can readily be appreciated using an electrically equivalent network representing the impedance seen at plane 13, comprised of a parallel $R_oLC$ network, driven by a perfect input transformer of turns ratio n:1. Here, L and C are the equivalent lumped inductance and capacitance, respectively, of dipole 21, and $R_o$ represents the effective lumped losses, primarily due to losses in heated material 7. The n:1 transformer represents inductive coupling between center conductor 6 and dipole 21 via circumferential gap 12. The resonant frequency is $$f_r = 1/[2\pi(LC)^{\frac{1}{2}}] \tag{1}$$

in which L is fixed due to the nonmagnetic properties of probe 30 and heated material 7. To a first order the capacitance C is given by $$C = C_o + K(\epsilon' - 1) \tag{2}$$

where $C_o$ is chiefly due to loading capacitors 22. The second term in Eq. (2) represents the effects of electric fields around dipole 21 which fringe into heated material 7, where K is a fringing constant. This term represents the effect of material 7 when it is something other than air ($\epsilon' = 1$). Since capacitors 22 have a large capacitance, $C_o/K >> 1$ with the result that $f_r$ in (1) is highly stable, irrespective of $\epsilon'$ of the surrounding material 7. Also, the large capacitance increase the quality factor ($Q = \omega_r C R_o$) of the resonant antenna. Finally, note that the $f_r$ is chiefly determined by $C_o$. While $C_o$ is dependent on the length $L_d$ of dipole 21 to some degree, $C_o$ is determined to a much greater degree by loading capacitors 22. Thus, the length $L_d$ is not fixed by the desired resonant frequency. Consequently, the desired active length of probe 30 can be chosen by design while keeping $f_r$ fixed.

The secondary resistance ($R_o$) of the equivalent $R_oLC$ network representing probe 30 includes the lumped effects of all losses. Since lossy material 7 is in close physical contact with probe 30, the dissipative losses of material 7 are dominant over the radiation and resistive losses of dipole 21. Assuming this to be the case, analysis shows that $$R_o = \frac{N\sqrt{C}}{\epsilon''} \quad (3)$$

where N is a constant and $\epsilon''$ is the loss factor of material 7. Thus, $R_o$ is essentially determined by $\epsilon''$, inversely.

At resonance, $R_o$ is transformed through the n:1 transformer representing inductive coupling through gap 12. When this transformed resistance is normalized by the characteristic resistance, $R_c$, of cable 1, the impedance mismatch or coupling factor at plane 13 is $$r_o = n^2 R_o/R_c = \frac{n^2 N\sqrt{C}}{R_c \epsilon''} \quad (4)$$

and is defined in terms of $\epsilon'$ (see Eq. (2)) and $\epsilon''$ of material 7. When $r_o = 1$, cable 1 is perfectly matched such that the reflected wave 26 and the reflection coefficient at plane 13 are zero, a condition known as "critical" coupling. When $r_o < 1$ the sensor is said to be "undercoupled," and it is "overcoupled" when $r_o > 1$. The well-known relationship between $r_o$ and the real reflection coefficient $\Gamma_r$ at plane 13 when the sensor is resonant at $f_r$ is $$\Gamma_r \text{ in dB} = 20 \log \left| \frac{r_o - 1}{r_o + 1} \right| \quad (5)$$

Note that when probe 30 is critically coupled at $f_r$, the magnitude of the complex reflection coefficient is $\Gamma_r = -\infty$ dB. In contrast, at frequencies far removed from $f_r$, the magnitude of the complex reflection coefficient is $|\Gamma| = 0$ dB, i.e., reflected wave 26 equals incident wave 25 in magnitude. Thus, $|\Gamma|$ dips to a very sharp minimum at $f_r$ when the probe is nearly critically coupled.

For practical use of the invention, $r_o$ in Eq. (4) should lie within a window which will always cause $\Gamma_r$ to be smaller than some desired value. For example, if $\Gamma_r$ is required to be less than $-10$ dB, then according to Eq. (5), $r_o$ must lie in the 4:1 window $0.5 < r_o < 2.0$. As seen from Eq. (4), the width of this window determines the range over which $\epsilon''$ can vary, e.g., 4:1. Then, to bring $r_o$ within the desired range, e.g., $0.5 < r_o < 2$, the turns ratio n in Eq. (4) is appropriately chosen.

As applied to various biological tissue, $\epsilon''$ generally varies less than a ratio of 4:1 so a good impedance match is assured. However, when probe 30 is in air ($\epsilon'' = 0$), the impedance match is very poor ($2 << r_o$) so there is little radiation into the environment.

By nature, dipole resonator 21 is usually overcoupled ($2 < r_o$) to gap 12, even when probe 30 is surrounded by material 7. There are several ways to reduce $r_o$:

a. by reducing the length $L_g$ of gap 12. In effect, this reduces the magnetic field coupling to dipole resonator 21. The practical limit is when the two sides of the gap nearly touch upon flexing probe 30.

b. by increasing the thickness, $t_{sub}$, of substrate 18. Again, this reduces the magnetic field coupling to dipole resonator 21. Here, the limit is the practical overall diameter of probe 30.

c. by adding a conducting coupling reducer or baffle 32 positioned symmetrically over gap 12 and under resonator 21. Baffle 32 is electrically insulated from resonator 21 and cable shield 1 by substrates 18 and 19 as shown in FIG. 1A. Baffle 32 can take several forms, such as a strip of conducting foil placed between substrates 18 and 19. The length $L_b$ of baffle 32 is typically substantially shorter than $L_d$ of resonator 21, and having a width $w_b$ less than $w_d$ of resonator 21. The function of baffle 32 is to reduce the exposure of resonator 21 to the driving electric field across gap 12 over an appreciable fraction of the width of resonator 21. An important advantage of this solution is that a prescribed, stable and reduced value of $r_o$ is achieved by choice of the width $w_b$ of baffle 32 in relation to the width $w_d$ of resonator 21, without significantly increasing the overall diameter of probe 30. In another form, baffle 32 could be a strip of dielectric film which is metalized on one side, while the opposing dielectric side serves as substrate 19 which is positioned around cable shield 2 and gap 12.

d. by connecting a resistive bridge 34 across gap 12 as shown in FIG. 3B. This resistive bridge 34 might take the form, for example, of a short segment of highly resistive wire or a thin film resistor, held in firm contact across gap 12 by heat-shrink dielectric substrate 18. Bridge 34 is placed at a position across gap 12 that is generally opposite the position of dipole resonator 21. When bridge 34 is used, its conductance $G_b$ is in parallel with $n^2 R_o$ of Eq. (4). Then, the mismatch or coupling factor $r_o$ of these parallel resistances at plane 13 becomes $$r_o = \frac{n^2 N\sqrt{C}}{R_c(n^2 N\sqrt{C}\, G_b + \epsilon'')} \quad (6)$$

so that $r_o$ in Eq. (6) using bridge 34 is less than $r_o$ in Eq. (4) without bridge 34. A disadvantage of bridge 34 is that it reduces the efficiency of probe 30 since significant power is lost in resistive bridge 34.

e. by moving dipole 21 along the axis of probe 30 so that the center of dipole 21 is offset from gap 12. Maximum coupling occurs when dipole 21 is centered over gap 12.

Any one or combination of methods a-e above can be effective in reducing the mutual coupling between dipole resonator 21 and gap 12 of probe 30 in FIG. 2.

Without conducting strip 27 in FIG. 1C and FIG. 2, there normally appear three hot spots along dipole 21. The largest hot spot is centered around the circumferential feed gap 12, and one each smaller hot spots appear near the ends of capacitors 22. Thus, there exists a region of minimum coupling between the feed region and the capacitor ends. Conducting strip 27 suppresses the hot spot at the center, and provides a path for power transmission from the feed gap region toward the ends of dipole 21. By making the length $L_s$ of strip 27 somewhat shorter than the length $L_d$ of dipole 21, power coupling to medium 7 is increased in the region of the minimum. As a result, power coupling to medium 7 is nearly uniform over the entire length of dipole 21, without excessive hot spot heating. Moreover, by translating strip 27 along the axis of probe 30, assymmetrical heating can be achieved if desired.

Besides insulating the metal component parts of probe 30, the first and second dielectric superstrates 23 and 33 serve another very important function. Without these dielectrics, the electric field coupled into lossy medium 7 would be radially directed, i.e., it would be normal to the conducting surfaces of dipole 21 and strip 27. This is dictated by the boundary condition that the tangential electric field must be zero on the surface of a good conductor. Since the magnetic field is transverse to the probe axis, the power in medium 7 would be forced to propagate along the axis of probe 30 as dictated by Poynting vector, $P = E \times H^*$. However, the presence of first and second superstrates 23 and 33 gives rise to a large longitudinal electric fields on the surface of superstrate 33. In fact, this longitudinal field is found to greatly exceed the radial electric field. Using Poynting's vector, the coupled power is seen to propagate radially outward from the axis of probe 30. Mapping of the amplitude and phase of electric fields around probe 30 shows them to be a radially directed propagating wave.

As might be expected, field maps also show some degree of directivity on the side where dipole 21 is positioned. To some degree, this directivity is determined by the circumferential width $w_d$ of dipole 21.

CONCLUSION AND SCOPE OF INVENTION

While the above description of the invention contains many specificities, these should not be construed as limitations on the scope of the invention. Rather, they are exemplifications of preferred embodiments. Many other variations and applications are possible, some of which are discussed below.

In the embodiment of probe 30 in FIG. 2, it is obvious that dipole resonator 21 could be replaced by some other shape, e.g., a cylinder, a bow tie, etc. Moreover, a method other than inductive coupling of the gap 12 to resonator 21 could be used, such as capacitive coupling between center conductor 6 and resonator 21. The use of gap 12 is preferred. However, because of its simplicity.

It would also be possible to position two or more dipole resonators on probe 30, each resonator having its own resonant frequency. In this manner, material 7 can be heated at two or more different microwave frequencies simultaneously, all fed by the same gap 12, to achieve desired heating patterns.

Dipole resonator 21 need not be centered over gap 12, but doing so maximizes coupling and avoids a resonant mode at twice the resonant frequency of the lowest order mode. Nonsymmetrical positioning of dipole 21 or strip 27 with respect to gap 12 may be an effective means for tapering of the coupled power deposition into material 7.

Figure 3A:
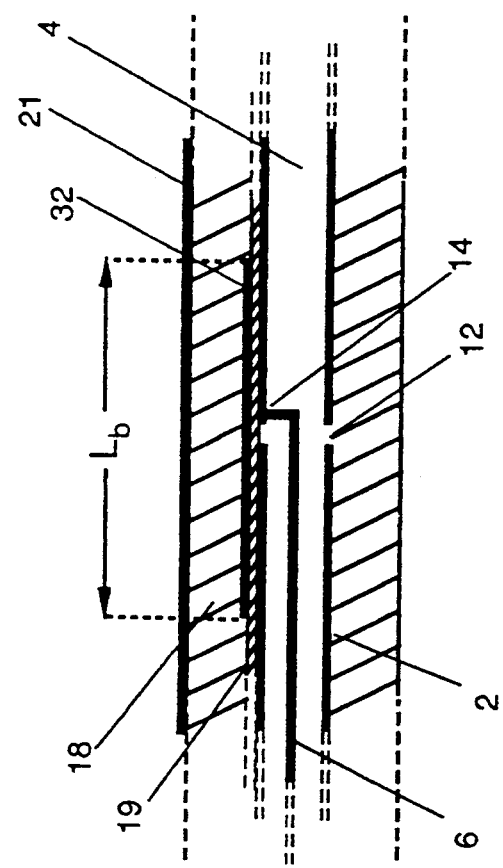

Desired coupling between gap 12 and dipole resonator 21 in probe 30 of FIG. 2 may be achieved by applying any one or combination of the methods a–e discussed under the Operation of the Invention heading. In particular, the use of a coupling reducer baffle 32 as shown in FIG. 3A is very effective for accomplishing a good impedance match (e.g., $0.5 < r_o\ 2.0$) when the invention is inserted into lossy material 7. This match can be accomplished without significantly increasing the diameter of probe 30, while still maintaining symmetry, high efficiency and simple, robust construction of the invention.

Superstrate 33 in probe 30 could be a catheter into which the assembly is inserted.

Capacitors 22 which load the ends of resonant dipole 21 in probe 30 of FIG. 2 need not be distributed; they could be discrete, lumped capacitors connected between the ends of dipole 21 and the shield 2 of coaxial cable 1.

There are several methods for inductively coupling coaxial center conductor 6 to circumferential gap 12 in FIGS. 1A, 1B, 1C, 2, 3A and 3E. As shown, center conductor 6 extends beyond gap 12 and is terminated in a zero impedance short to cable shield 2 at point 14, which is the preferred embodiment. However, center conductor 6 could be terminated in any impedance which gives the desired coupling to gap 12. For example, center conductor 6 could extend beyond gap 12 a distance of an odd multiple of quarter wavelengths at the resonant frequency and be terminated in an open circuit. This arrangement would yield an equivalent short circuit at the location of gap 12. More generally, center conductor 6 could be terminated by any of many suitable load impedances beyond gap 12, provided center conductor 6 extends beyond gap 12 by an appropriate distance so that such a load impedance is transformed into the desired impedance at gap 12. For example, a resistive load located one quarter wavelength beyond gap 12 would determine the magnitude of the magnetic field and hence the coupling factor $r_o$ at gap 12. Such a termination would reduce the coupling factor $r_o$, and could replace bridge 34 in FIG. 3B which serves a similar function. Whatever the terminating arrangement used, it is generally undesirable to have a net non-zero reactance at reference plane 13 at the true resonant frequency of the resonator ($f_r$) since such a reactance would alter the observed resonant frequency at plane 13.

Coaxial cable 1 need not be rigid or semi-rigid. In fact, the entire assembly 30 in FIG. 2 can be flexible.

Use of probe 30 in FIG. 2 is not restricted to biological tissue, and can be used in many types of "soft" materials (e.g., flakes, powders or liquids) into which probe 30 can easily be inserted. The invention could even be embedded in solids. For example, the outer dielectric sheath (superstrate 33 in FIG. 2) could be permanently embedded in a solid, and the remainder of probe assembly 30 could be inserted into the embedded dielectric sheath whenever desired.

Accordingly, the scope of the invention should be determined not by the embodiments illustrated but by the appended claims and their legal equivalents.

We claim:

1. A microwave resonator heat applicator probe for selective deposition of microwave power and heating patterns in lossy dielectric materials, comprising:
   a coaxial cable having a metal shield and center conductor;
   a short circumferential gap in the metal shield of the coaxial cable, the center conductor of the coaxial cable extending immediately beyond the gap, and then shorted to the cable shield;
   a thin dielectric substrate sheath covering the cable shield and the gap;
   a thin conductive dipole resonator placed on the substrate sheath and positioned near the gap to facilitate inductive coupling between the gap and the resonator;
   capacitive terminations at the ends of the conductive dipole resonator, formed by widening the ends of the resonator and reducing the dielectric substrate to a very thin insulator between the widened resonator ends and the coaxial cable shield;
   a thin first dielectric superstrate sheath covering the conductive dipole resonator and capacitive terminations;

a thin conductive strip placed on the first dielectric superstrate and extending parallel to the dipole resonator so as to partially cover the resonator;

a thin second dielectric superstrate sheath covering the entire probe assembly.

2. A microwave resonator heat applicator probe for selective deposition of microwave power and heating patterns in lossy dielectric materials, comprising:

a coaxial cable having a metal shield and center conductor:

a short circumferential gap in the metal shield of the coaxial cable, the center conductor of the coaxial cable extending immediately beyond the gap and then shorted to the cable shield;

a thin dielectric substrate covering the cable shield and gap;

a conductive resonator placed on the substrate sheath and positioned near the gap to facilitate inductive coupling between the gap and the resonator;

capacitive loading between the resonator and the cable shield.

3. The microwave resonator probe of claim 2 wherein the resonator is a thin conductive dipole.

4. The microwave resonator probe of claim 3 wherein the capacitive loading is formed by widening the ends of the dipole resonator, reducing the dielectric substrate to a very thin dielectric insulator between the widened resonator ends and the coaxial cable shield, and wrapping the widened ends of the resonator around the thus insulated cable shield.

5. The microwave resonator probe of claim 2 wherein the capacitive loading comprises discrete lumped capacitors.

6. The microwave resonator probe of claim 2 further comprising a thin first dielectric superstrate sheath covering the resonator and capacitive loading.

7. The microwave resonator probe of claim 6 further comprising a thin conductive strip placed on the first dielectric superstrate so as to partially cover the resonator and distribute the power uniformly along the resonator.

8. The microwave resonator probe of claim 7 further comprising an enclosing second dielectric superstrate sheath.

9. The microwave resonator probe of claim 8 in which the second dielectric superstrate sheath comprises a catheter into which the probe can be inserted.

10. The microwave resonator probe of claim 2 further comprising a source of microwave power at the resonant frequency of the resonator probe, such power being sufficient to locally heat a lossy dielectric material to a desired temperature.

11. The microwave resonator probe of claim 2 further comprising a conductive coupling reducer or baffle positioned between and electrically insulated from the resonator and the coaxial cable shield, said coupling reducer or baffle producing a desired impedance matching factor.

12. The microwave resonator of claim 2 further comprising a resistive bridge electrically connected across the gap for producing the desired impedance matching factor, or for reducing the sensitivity of the matching factor to the loss factor of the lossy heated material, or both.

13. A microwave resonator heat applicator probe for selective deposition of microwave power and heating patterns in lossy dielectric materials at two or more frequencies, comprising:

a coaxial cable having a metal shield and center conductor;

a short circumferential gap in the metal shield of the coaxial cable, the center conductor of the coaxial cable extending immediately beyond the gap and then shorted to the cable shield;

a thin dielectric substrate sheath covering the cable shield and gap;

one or more thin conductive dipole resonators placed on the substrate sheath, each resonator resonating at a different resonant frequency, all of the resonators being electrically insulated from each other and positioned near the gap to facilitate inductive coupling between the gap and all of the resonators at the resonant frequency of each resonator;

capacitive terminations between the ends of the each dipole resonator and the cable shield;

a thin first dielectric superstrate sheath covering the resonators and capacitive terminations;

one or more thin conductive strips placed on the first dielectric superstrate and extending parallel to the resonators so as to partially cover the resonators;

a thin second dielectric superstrate sheath covering the entire probe assembly.

14. A microwave resonator heat applicator probe for selective deposition of microwave power and heating patterns in lossy dielectric materials, comprising:

a coaxial cable having a metal shield and center conductor;

a thin dielectric substrate sheath covering the cable shield;

a conductive resonator placed on the substrate sheath;

capacitive loading between the resonator and the cable shield for reducing the physical length of the resonator;

an electrical feed means for coupling power from the coaxial cable to the resonator at the resonant frequency of the resonator.

15. The microwave resonator probe of claim 14 wherein the electrical feed means includes a short circumferential gap in the coaxial cable shield, the center conductor of the coaxial cable extending immediately beyond the gap, and then shorted to the cable shield to achieve inductive coupling between the coaxial cable and the resonator.

16. The microwave resonator probe of claim 14 wherein the electrical feed means includes an extension of the center conductor of the coaxial cable through an insulated hole in the cable shield and dielectric substrate, and connection of the extended center conductor to the resonator.

17. The microwave resonator probe of claim 14 wherein the electrical feed means includes an extension of the center conductor of the coaxial cable through a hole in the cable shield and dielectric substrate, and capacitive coupling of the extended center conductor to the resonator.

18. The microwave resonator probe of claim 14 further comprising a thin first dielectric superstrate sheath covering the metal resonator and capacitive loading.

19. The microwave resonator probe of claim 14 wherein the electrical feed means includes a short circumferential gap in the coaxial cable shield, an extension of the center conductor of the coaxial cable beyond the gap, and termination of the cable beyond the gap in an impedance which is selected to achieve a desired input impedance matching factor.

20. A method for selective deposition of microwave power patterns in lossy dielectric materials, comprising:

forming a short circumferential gap in the shield of a coaxial cable having a connector at one end;

extending the cable center conductor immediately beyond the gap and then shorting the center conductor to the cable shield:

enclosing the gap and the cable within a thin dielectric substrate sheath;

placing a conductive resonator on the dielectric substrate sheath:

positioning the resonator near the gap to facilitate inductive coupling between the gap and the resonator;

enclosing the cable, substrate sheath and resonator within a dielectric superstrate sheath to form the completed probe;

inserting the completed probe into a lossy dielectric material to be heated;

connecting a source of microwave power to the cable connector, the frequency of the microwave source being equal to the resonant frequency of the completed probe and the power being sufficient to locally heat the lossy material to a desired temperature.

21. The method of claim 20 further comprising the use of capacitive loading between the resonator and the cable shield.

22. The method of claim 20 wherein the resonator is formed as a thin conductive dipole resonator.

23. The method of claim 19 further comprising placement of a conductive coupling reducer or baffle between, and electrically insulated from, the resonator and the coaxial cable shield, said coupling reducer or baffle producing a desired impedance matching factor.

24. The method of claim 20 further comprising placement of a conductive strip on the dielectric superstrate sheath so as to partially cover the resonator and distribute the power uniformly along the resonator.

25. The method of claim 24 further comprising enclosing the conductive strip, superstrate sheath, resonator, substrate and cable within a second dielectric superstrate sheath to form the completed probe.

* * * * *